United States Patent
Fateh et al.

(10) Patent No.: US 10,548,765 B2
(45) Date of Patent: Feb. 4, 2020

(54) UNIVERSAL MODULAR ATTACHMENTS FOR EYE DROP CONTAINERS

(71) Applicant: Kali Care, Inc., Mountain View, CA (US)

(72) Inventors: Sina Fateh, Mountain View, CA (US); Philippe Cailloux, Sunnyvale, CA (US)

(73) Assignee: KALI CARE, INC., Santa Clara, CA (US)

( * ) Notice: Subject to any disclaimer, the term of this patent is extended or adjusted under 35 U.S.C. 154(b) by 0 days.

(21) Appl. No.: 15/618,518

(22) Filed: Jun. 9, 2017

(65) Prior Publication Data

US 2018/0353327 A1    Dec. 13, 2018

(51) Int. Cl.
*A61F 9/00* (2006.01)
*H04Q 9/00* (2006.01)

(52) U.S. Cl.
CPC ............ *A61F 9/0008* (2013.01); *H04Q 9/00* (2013.01); *H04Q 2209/40* (2013.01)

(58) Field of Classification Search
CPC ........ A61F 9/0008; B65D 25/20; H04Q 9/00; H04Q 2209/40
See application file for complete search history.

(56) References Cited

U.S. PATENT DOCUMENTS

| | | | |
|---|---|---|---|
| 8,807,131 B1 * | 8/2014 | Tunnell | A61M 16/0051 128/200.23 |
| 9,218,458 B2 | 12/2015 | Baarman et al. | |
| 9,728,068 B2 * | 8/2017 | Engelhard | H05K 999/99 |
| 2006/0124655 A1 | 6/2006 | Ratnakar | |
| 2008/0114490 A1 * | 5/2008 | Jean-Pierre | G06F 19/00 700/241 |
| 2011/0253139 A1 * | 10/2011 | Guthrie | A61M 15/009 128/203.14 |
| 2014/0251850 A1 | 9/2014 | Huang et al. | |
| 2014/0276476 A1 * | 9/2014 | Fateh | G08B 21/02 604/290 |
| 2015/0359667 A1 * | 12/2015 | Brue | A61F 9/0008 604/295 |
| 2017/0109498 A1 * | 4/2017 | Childress | G06F 19/3462 |
| 2018/0114415 A1 * | 4/2018 | Mattingly | G08B 7/02 |

* cited by examiner

*Primary Examiner* — James J Yang
*Assistant Examiner* — Kevin Lau
(74) *Attorney, Agent, or Firm* — Perkins Coie LLP

(57) ABSTRACT

Introduced here are universal modular attachments that can be attached to medication containers. Because a single modular attachment is typically attachable to medication containers of different sizes, the modular attachment can be referred to as a "universal modular attachment." For example, some universal modular attachments are attachable to any cylindrical eye drop container having a diameter ranging from 20 millimeters (mm) to 27 mm. A connector ring that substantially matches the diameter of the medication container secures the universal modular attachment to the medication container. The connector ring may be fixedly affixed to the medication container, while the universal modular attachment may be detachably connectable to the connector ring. Each universal modular attachment also includes sensor(s) that are configured to detect administrations of medication. For example, the universal modular attachment may include a motion sensor able to detect instances of movement that are indicative of administrations of medication.

26 Claims, 8 Drawing Sheets

UNIVERSAL MODULAR ATTACHMENTS FOR EYE DROP CONTAINERS

RELATED FIELD

Various embodiments concern network-connected (i.e., "smart") modular attachments that detect and track administrations of medication from a medication container.

BACKGROUND

Approximately thirty percent of medication prescriptions are never filled, and nearly fifty percent of medications for chronic diseases (i.e., long-lasting conditions) are not taken as prescribed. This lack of adherence to medication regimens has dramatic effects on the health of individuals and the healthcare costs for society as a whole. Non-adherence has been estimated to cost the U.S. health care system $200 billion annually.

For example, compliance with an opthalmological medication plan (also referred to as a "medication regimen") may be vital for preventing visual loss and blindness resulting from chronic conditions such as glaucoma. But almost seventy-five percent of patients admit to some form of noncompliant behavior, over thirty percent of patients do not fill their prescriptions, and nearly fifty percent of patients discontinue their prescriptions within six months of it being prescribed.

While forgetfulness is one barrier to adherence with a medication regimen, it is not the only barrier. Taking the medication at the wrong time, stopping administration of the medication too early, and taking the wrong dose also represent serious barriers to adherence. Unfortunately, there are no effective systems for managing adherence to a medication regimen that may be necessary to maintain or improve an individual's health in a convenient and inconspicuous manner.

BRIEF DESCRIPTION OF THE DRAWINGS

Embodiments of various universal modular attachments (also referred to as "the technology") are illustrated by way of example and not limitation in the accompanying drawings, in which like references indicate similar elements. Various objects, features, and characteristics of the technology will become more apparent to those skilled in the art from a study of the Detailed Description in conjunction with the accompanying drawings.

Figure 1:
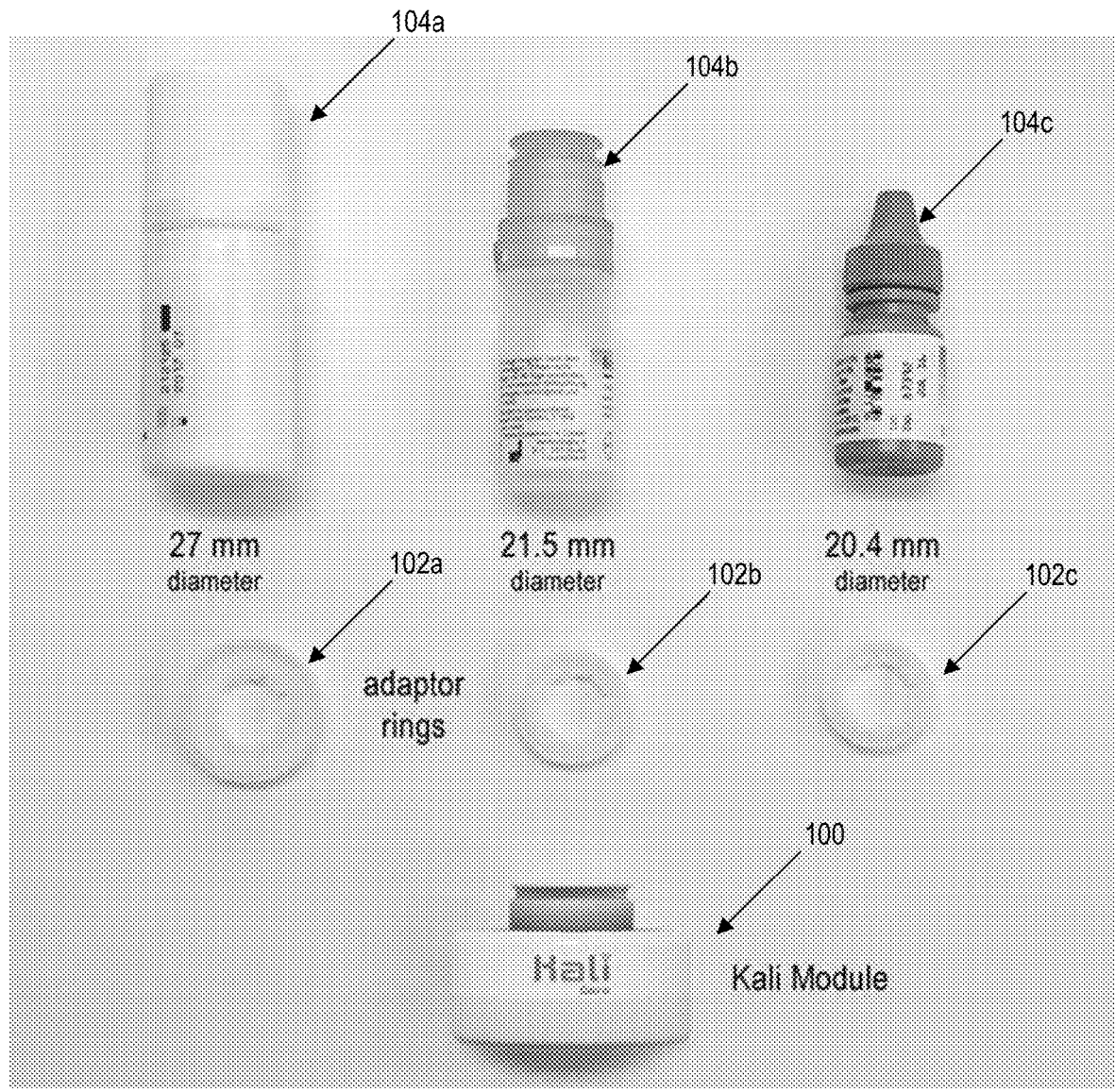
FIG. 1 depicts a universal modular attachment that can be secured to any of several eye drop containers.

The figures depict various embodiments of the technology for the purpose of illustration only. Those skilled in the art will recognize that alternative embodiments may be employed without departing from the principles of the technology.

DETAILED DESCRIPTION

A medication regimen is a plan or a regulated course of action(s) (e.g., diet and exercise) that is designed to improve or maintain the health status of a person. For example, a medication regimen may identify a medication that is to be administered by an individual, the frequency and/or time that dose(s) of the medication are to be administered, the amount/quantity of each dose, etc.

There are many reasons why an individual may not comply with a medication regimen. For example, the individual may forget to administer the medication, misunderstand the medication regimen, make an error regarding the dose (e.g., the amount/quantity or time), forget to refill a prescription, or could simply be unable to afford the medication. But the lack of adherence may have a severe impact on the individual's health.

Moreover, there may be a number of parties who have a vested interest in whether the individual adheres to the medication regimen. Interested parties could include family members, healthcare personnel (e.g., physicians, nurses, and pharmacists), researchers, pharmaceutical developers, etc. For example, a child of an elderly parent may want to know when the parent has failed to adhere to a medication regimen so that the child can identify the reason(s) for the non-adherence and take appropriate action(s).

Introduced here, therefore, are modular attachments for managing the administration of a medication from a medication container, such as an eye drop container. More specifically, the modular attachments can be connected to medication containers using connector rings. Because a single modular attachment is typically attachable to multiple eye drop containers of different sizes, the modular attachment can be referred to as a "universal modular attachment" or a "universal attachment."

A universal modular attachment can include one or more sensors (e.g., motion sensors, pressure sensors, positional sensors) that enable the universal modular attachment to readily monitor adherence to a medication regimen. For example, the universal modular attachment may examine motion data generated by a motion sensor to detect acts indicative of an administration of medication (e.g., shaking or tilting). Accordingly, the technology can be used to address a fundamental challenge, namely, accurately tracking usage of an eye drop container in a convenient and inconspicuous manner.

For example, some embodiments of the universal modular attachment are attachable to any cylindrical eye drop container having a diameter ranging from 20 millimeters (mm) to 27 mm. A connector ring that substantially matches the diameter of each eye drop container can be used to secure the universal modular attachment to the corresponding eye drop container. Thus, eye drop containers of different sizes may be connected to connector rings of different sizes, while each connector ring (regardless of size) may be designed to interface with the universal modular attachment. A connector ring can be fixedly affixed to a corresponding eye drop container through the use of permanent/semi-permanent adhesives, fixtures, ultrasonic welding, etc.

A universal modular attachment can then be detachably connected to the connector ring through the use of a quick release mechanism (e.g., magnets or mechanical clips/features). For example, an individual may secure the universal modular attachment to the connector ring by aligning complementary magnets, physical male threads that are designed to mate with complementary female threads, etc. Such a design allows the individual to remove the universal modular attachment from the connector ring affixed to an empty eye drop container, and then attach the universal modular attachment to another connector ring affixed to a full eye drop container. The connector ring can simply be thrown away along with the empty eye drop container.

The universal modular attachment could include one or more sensors that enable administrations of medication to be detected. Various embodiments could include an electromagnetic sensor, motion sensor, positional sensor, sound sensor (e.g., microphone), optical sensor (e.g., camera), climate sensor (e.g., humidity sensor, temperature sensor, or smog sensor), and/or a pressure sensor. Those skilled in the art will recognize that a universal modular attachment could include some or all of these sensors, as well as other sensors. For example, some embodiments of the universal modular attachment include a motion sensor that indicates when the eye drop container is being tilted or shaken. As another example, some embodiments of the universal modular attachment include a pressure sensor that detects deformations in the housing of the eye drop container due to squeezing. In such embodiments, the pressure sensor may be disposed along the top of the universal modular attachment such that it maintains contact with the bottom side of the eye drop container, or the pressure sensor could be affixed along the sidewall of the eye drop container (e.g., disposed beneath the label sticker of the eye drop container).

Data generated by the sensor(s) can be used to track adherence to a medication regimen and generate an adherence report. The universal modular attachment may transmit some or all of the data to another computing device (e.g., a mobile phone) associated with the individual, a network-accessible storage, or both. Consequently, the individual may be able to view the adherence report (as well as related recordings and other information) via an interface presented by a web browser, desktop software program, mobile application, or over-the-top (OTT) application. The interface may be accessible via a mobile phone, tablet computer, personal computer, game console (e.g., Sony PlayStation® or Microsoft Xbox®), wearable electronic device (e.g., a watch or fitness tracker), network-connected ("smart") devices, virtual/augmented reality systems (e.g., Oculus Rift® or Microsoft Hololens®), etc. Additionally or alternatively, the interface may be accessible via a display included in the universal modular attachment or a display included in the eye drop container. The display could present various types of information regarding the medication, medication regimen, compliance status, etc.

Embodiments have been described in the context of certain types of medication, (e.g., eye drops), containers (e.g., cylindrical bottles), and networks (e.g., Bluetooth®) for the purpose of illustration only. Those skilled in the art will recognize that the features described herein are equally applicable to other types of medications, containers, networks, etc.

Moreover, the technology can be embodied as special-purpose hardware (e.g., circuitry), programmable circuitry appropriately programmed with software and/or firmware, or as a combination of special-purpose hardware and programmable circuitry. Accordingly, embodiments may include a machine-readable medium having instructions that may be used to program a computing device to perform a process for parsing sensor data to detect administrations of medication, monitor compliance with a medication regimen, etc.

Terminology

Brief definitions of terms, abbreviations, and phrases used throughout the specification are given below.

Reference in this specification to "one embodiment" or "an embodiment" means that a particular feature, structure, or characteristic described in connection with the embodiment is included in at least one embodiment of the disclosure. The appearances of the phrase "in some embodiments" are not necessarily referring to the same embodiments, nor are they necessarily referring to separate or alternative embodiments that are mutually exclusive of one another. Various features are described that may be exhibited by some embodiments but not others. Similarly, various requirements are described that may be requirements for some embodiments but not others.

Unless the context clearly requires otherwise, the words "comprise" and "comprising" are to be construed in an inclusive sense rather than an exclusive or exhaustive sense (i.e., in the sense of "including, but not limited to"). The terms "connected," "coupled," or any variant thereof includes any connection or coupling between two or more elements, either direct or indirect. The coupling or connection between the elements can be physical, logical, or a combination thereof. For example, devices may be coupled directly to one another or via one or more intermediary channels/devices. Devices may also be coupled in such a way that information can be passed there between, despite not sharing any physical connection with one another. The words "associate with," meanwhile, mean connecting or relating objects, items, etc.

Where the context permits, words used in the singular sense or the plural sense may also be used in the plural sense or the singular sense, respectively. The word "or," in reference to a list of two or more items, covers all of the following interpretations of the word: any of the items in the list, all of the items in the list, and any combination of the items in the list. If the specification states a component or feature "may," "can," "could," or "might" be included or have a characteristic, that particular component or feature is not required to be included or have the characteristic in every embodiment.

The term "module" refers broadly to software, hardware, and/or firmware components. A module is typically a functional software component that can generate useful data or other output using specified input(s). A module may or may not be self-contained. A software program or a mobile application may include one or more modules.

The terminology used in the Detailed Description is intended to be interpreted in its broadest reasonable manner, even though it is being used in conjunction with certain embodiments. The terms used in this specification generally have their ordinary meanings in the art, in the context of the disclosure as a whole and in the specific context where each term is used. For convenience, certain terms may be highlighted using, for example, capitalization, italics, and/or quotation marks. However, the use of highlighting has no influence on the scope and meaning of a term. The scope and meaning of a term is the same, in the same context, whether or not it is highlighted.

Although alternative language and synonyms may be used for some terms, special significance is not to be placed upon whether or not a term is elaborated or discussed herein. A recital of one or more synonyms does not exclude the use of other synonyms. The use of examples anywhere in this specification, including examples of any terms discussed herein, is intended to be illustrative only. The examples are not intended to limit the scope and meaning of the disclosure or of any exemplified term. Likewise, the disclosure is not limited to the various embodiments described below.

System Topology Overview

FIG. 1 depicts a universal modular attachment 100 that can be secured to any of several eye drop containers 104a-c. The physical modular attachment can be referred to as a "universal modular attachment" because it is typically attachable to multiple eye drop containers of different sizes. Here, for example, the universal modular attachment 100 can be secured to eye drop containers 104a-c of various sizes using corresponding connector rings 102a-c (also referred to as "adaptor rings").

In some embodiments, the universal modular attachment 100 is attachable to any cylindrical eye drop container having a diameter ranging from 20 mm to 27 mm. However, other embodiments of the universal modular attachment 100 can be designed such that they can be affixed to cylindrical medication containers smaller or larger than this. Similarly, some embodiments of the universal modular attachment 100 are designed such that they can be affixed to non-cylindrical medication containers.

Each connector ring 102a-c can substantially match the diameter of the base of a corresponding eye drop container 104a-c. Thus, different sizes of connector ring sizes may exist for different sizes of medication container. In some embodiments, the connector ring 102a-c is fixedly attached to the eye drop container 104a-c through the use of permanent/semi-permanent adhesives, fixtures (e.g., screws), ultrasonic welding, etc. For example, the connector ring 102a-c could be secured to the eye drop container 104a-c by a label sticker that extends along the outer surfaces of the eye drop container 104a-c and the connector ring 102a-c.

Figure 2:
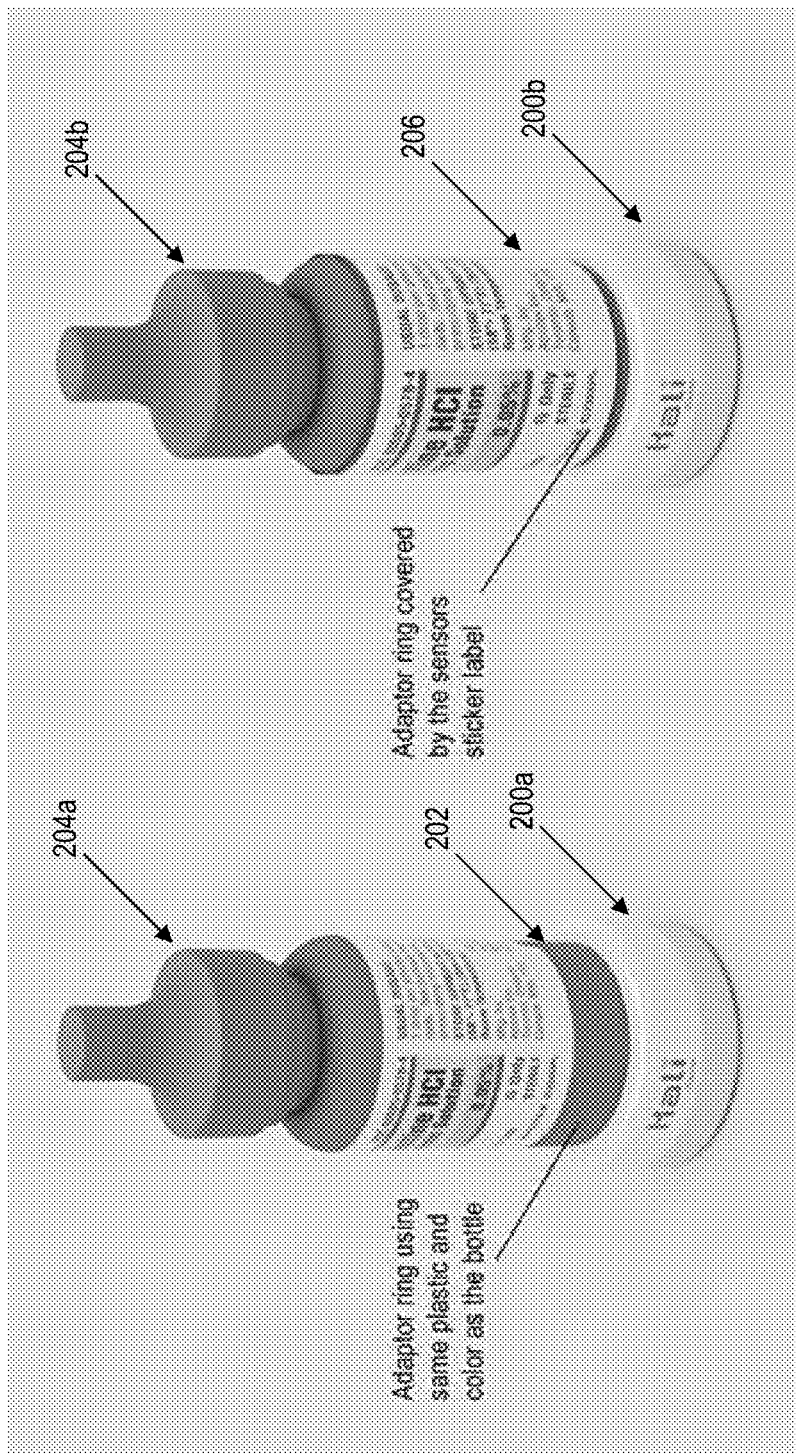
FIG. 2 depicts universal modular attachments that have been connected to eye drop containers using connector rings.

FIG. 2 depicts universal modular attachments 200a-b that have been connected to eye drop containers 204a-b using connector rings 202. More specifically. FIG. 2 depicts a first embodiment where a universal modular attachment 200a has been connected to a connector ring 202 that shares certain characteristic(s) with the eye drop container 204a, such as material composition and color, and a second embodiment where the universal modular attachment 200b has been connected to a connector ring disposed beneath a label sticker 206 that is affixed to the sidewall of the eye drop container 204b. The adhesive side of the label sticker 206 can simply be affixed to the outer surface of the connector ring, thereby further securing the connector ring against the bottom side of the eye drop container 204b.

In some embodiments, the label sticker 206 includes one or more sensors that are operatively/communicatively coupled to the universal modular attachment 200b. For example, the label sticker 206 could include pressure sensor(s) (e.g., capacitive tactile pressure sensors) that are configured to detect when an individual grasps the eye drop container 204b and/or the connector ring. As another example, the label sticker 206 could include pressure sensor(s) (e.g., piezoelectric sensors) that generate an electronical signal upon being deformed due to the individual squeezing the eye drop container 204b (and thus deforming the housing of the eye drop container 204b). The sensor(s) are typically disposed beneath, or embedded within, the label sticker 206 that is affixed to the outer surface of the housing of the eye drop container 204b. However, those skilled in the art will recognize that the sensor(s) could also be connected to, or embedded within, the housing of the eye drop container 204b.

The sensor(s) can carry signals down to an adaptor interface of the universal modular attachment 200a-b. The universal modular attachment 200a-b may use the signals (or a certain subset thereof) to trigger certain actions. For example, the universal modular attachment 200b may activate a motion sensor or a positional sensor upon receiving a signal indicating that the individual has grasped the eye drop container 204b and applied pressure to a pressure sensor disposed beneath the label sticker 206.

The connector ring 202 is typically comprised of plastic, rubber, metal, or some other suitable material that is inexpensive, durable, and readily molded. Such a design allows the individual to readily dispose of the eye drop container 204a-b (including any label sticker(s) 206) and the connector ring 202 when the eye drop container 204a-b is empty. The universal modular attachment 200a-b, meanwhile, can be reused and affixed to another connector ring attached to another eye drop container.

Figure 3:
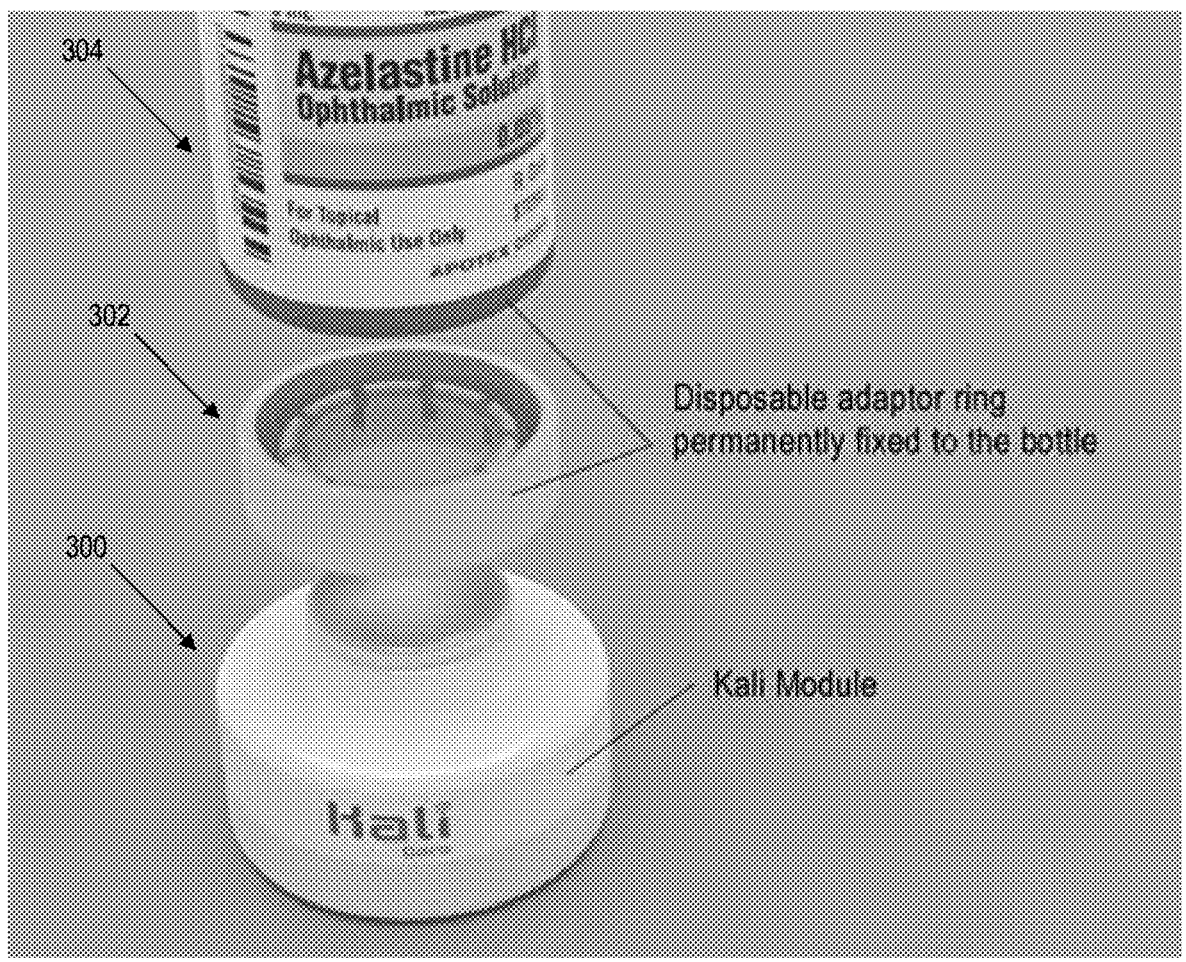
FIG. 3 depicts an exploded view of a universal modular attachment, a connector ring, and an eye drop container.

FIG. 3 depicts an exploded view of a universal modular attachment 300, a connector ring 302, and an eye drop container 304.

The universal modular attachment 300 may be detachably connectable from the connector ring 302 through the use of a quick release mechanism (e.g., magnets or mechanical clips/features). For example, an individual may secure the universal modular attachment 300 to the connector ring 302 by aligning complementary magnets, physical male threads that are designed to mate with complementary female threads, etc. Such a design allows the individual to readily remove the universal modular attachment 300 from the connector ring affixed to an empty eye drop container, and then attach the universal modular attachment 300 to another connector ring affixed to a full eye drop container.

Because the connector ring 302 is generally comprised of a disposable material (e.g., plastic, rubber, or metal), the connector ring 302 can be permanently fixed to disposable eye drop containers. Some embodiments of the connector ring 302 are comprised of food grade material(s) and/or water-resistant material(s). The connector ring 302 may further comprise a smooth powder coating that provides a durable aesthetic finish. The connector ring 302 and/or the powder coating may include an antimicrobial additive that inhibits the growth and development of microorganisms.

Feature(s) of the connector ring 302 could also be incorporated into the universal modular attachment 300 and/or the eye drop container 304. For example, complementary mating components may be included on the housing of the universal modular attachment 300 and the housing of the eye drop container 304. In such embodiments, the universal modular attachment 300 and the eye drop container 304 can interface directly with one another, thereby rendering a separate connector ring 302 unnecessary.

Figure 4:
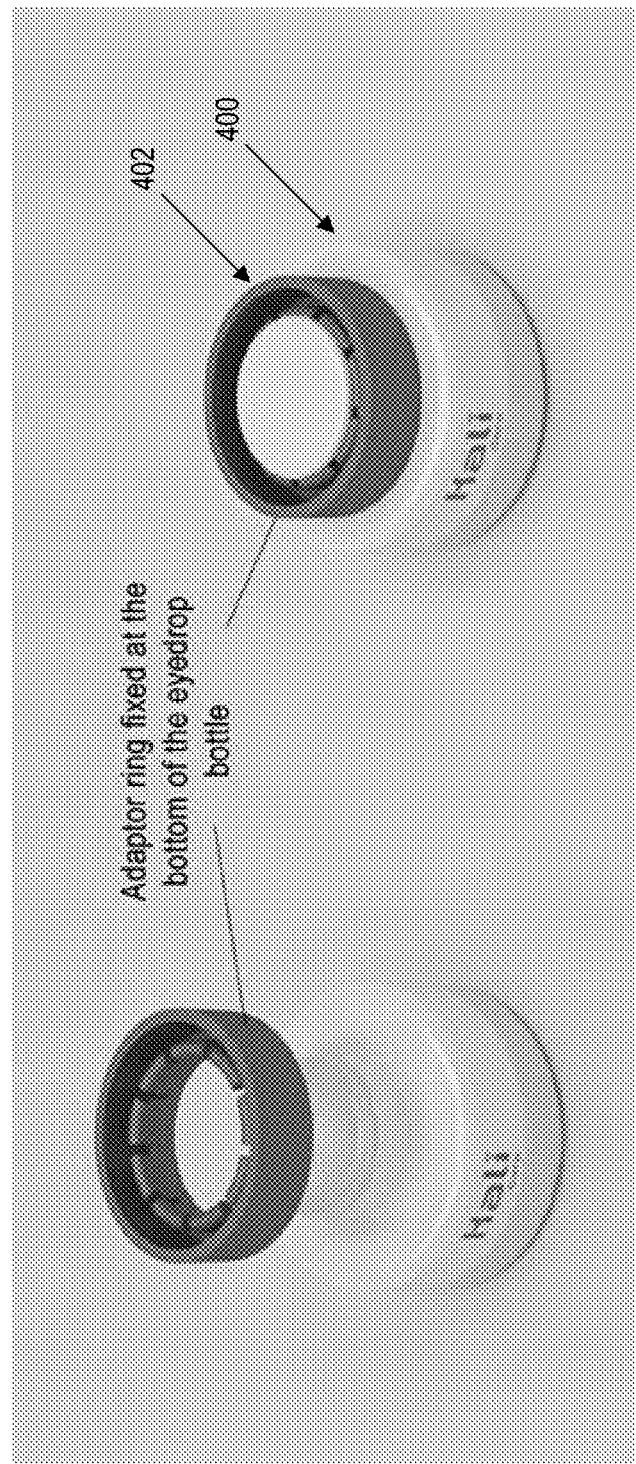
FIG. 4 illustrates how a connector ring can securably receive a portion of a universal modular attachment.

FIG. 4 illustrates how a connector ring 402 can securably receive a portion of a universal modular attachment 400. Here, for example, the connector ring 402 includes a series of physical teeth that engage a head of the housing of the universal modular attachment 400. Some embodiments of the connector ring 402 include a tab that can be depressed to release the series of physical teeth so that the universal modular attachment 400 can be removed. Other embodiments of the connector ring 402 instead design/manufacture the physical teeth such that the universal modular attachment 400 can be removed upon being tugged/pulled.

The connector ring 402 may also enable signal(s) to be carried from sensor(s) disposed beneath, or embedded within, the label sticker of an eye drop container down to an adaptor interface of the universal modular attachment 400. For example, two signals can be carried to the universal modular attachment 400 from a pressure sensor disposed beneath the label sticker, and one of those signals can be duplicated to create a third signal that indicates when the universal modular attachment 400 is snapped to the connector ring 402. As another example, two signals can be carried to the universal modular attachment 400 from a pressure sensor disposed beneath the label sticker, and a separate signal can be carried to the universal modular attachment 400 from a sensor (e.g., a piezoresistive strain gauge, mechanical pressure switch, or optical sensor) that detects when the universal modular attachment 400 has been snapped to the connector ring 402. Such a sensor could be disposed within the connector ring 402 or on a portion of the universal modular attachment 400 that interfaces with the connector ring 402.

When the eye drop container is empty, the individual can remove the universal modular attachment 400 by disconnecting it from the connector ring 402. The universal modular attachment 400 and the connector ring 402 are typically designed such that the individual can simply tug on the universal modular attachment 400 to remove it. The individual can then discard the empty eye drop container along with the label sticker and the connector ring 402. The universal modular attachment 400 is typically designed such that it can be reused and connected to multiple eye drop containers (e.g., tens or hundreds of eye drop containers) over its lifetime.

While the universal modular attachment 400 should be easy to connect to and disconnect from the connector ring 402, the universal modular attachment 400 should remain affixed to the connector ring 402 during normal use/travel. For instance, the universal modular attachment 400 and the connector ring 402 can be designed and manufactured with sufficient precision that they remain connected when carried in a purse, backpack, etc.

Figure 5:
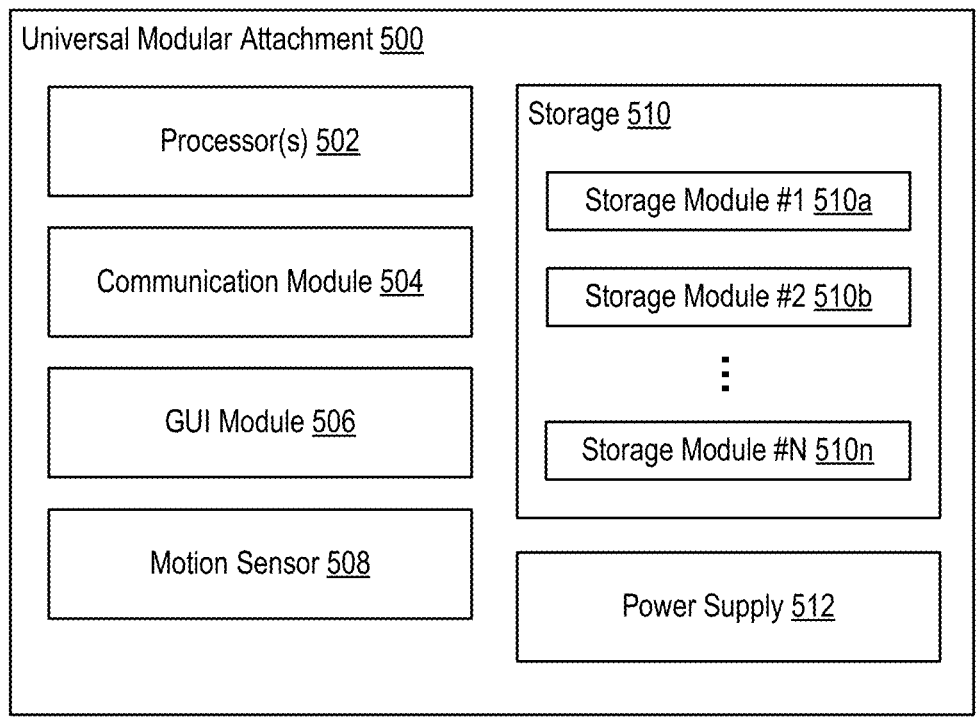
FIG. 5 is a block diagram of a universal modular attachment that is configured to track administrations of medication.

FIG. 5 is a block diagram of a universal modular attachment 500 that is configured to track administrations of medication. The universal modular attachment 500 can include one or more processors 502, a communication module 504, a graphical user interface (GUI) module 506, a motion sensor 508, a storage medium 510, and a power supply 512.

Other embodiments of the universal modular attachment 500 may include some or all of these modules/components, as well as other modules/components such as an electromagnetic sensor, a positional sensor, a sound sensor (e.g., a microphone), a climate sensor (e.g., humidity sensor, temperature sensor, or smog sensor), pressure sensor, etc. For example, some embodiments of the universal modular attachment 500 include electromagnetic sensor(s) that are configured to detect/identify variations in electromagnetic radiation in the ambient environment.

The processor(s) 502 can execute the modules from instructions stored in the storage medium 510, which can be any device or mechanism capable of storing information. Communication module 504 may manage communications between components of the universal modular attachment 500 and/or between the universal modular attachment 500 and another computing device. For example, the communication module 504 may transmit motion data generated by the motion sensor 508 to a network-accessible server system or a computing device associated with an individual for further review. Thus, the communication module 504 can effect a unidirectional transmission of information to another computing device across a network or a bidirectional exchange of information with another computing device across a network. The motion data generated by the motion sensor 508 can be stored in the storage medium 510, one or more particular storage modules (e.g., storage modules 510a-n), a remote network-accessible storage, or some combination thereof.

The GUI module 506 can generate an interface that allows the individual to interact with universal modular attachment 500, review data generated by the sensor(s), etc. In some embodiments, the GUI module 506 is executed by another computing device. For example, a computing device (e.g., a mobile phone) associated with the individual may include a mobile application that executes the GUI module 506. In such embodiments, the GUI module 506 need not reside on the universal modular attachment 500.

The motion sensor 508 can detect movement of the universal modular attachment 500. Because the universal modular attachment 500 is connected to an eye drop container, the processor(s) 502 can parse motion data generated by the motion sensor 508 to detect when the eye drop container is being tilted or shaken. Such actions typically correspond to administrations of medication, and thus can be used to monitor adherence to a medication regimen. As noted above, other embodiments of the universal modular attachment 500 may include other sensor(s). For example, some embodiments of the universal modular attachment 500 are connected to a pressure sensor that detects deformations in the housing of the eye drop container. The pressure sensor may be disposed along the top of the universal modular attachment 500 such that it maintains contact with the bottom side of the eye drop container, or it could be affixed along the sidewall of the eye drop container (e.g., arranged beneath the label sticker of the eye drop container).

The sensor(s) can be activated/deactivated in several ways. For example, some embodiments include a physical on/off switch, while other embodiments include a sound sensor (e.g., a microphone) or a light sensor (e.g., a camera) configured to detect activation utterances and gestures, respectively. Other examples of activation/deactivation trigger mechanisms include sensing pressure (e.g., via the pressure sensors disposed beneath the label sticker of the eye drop container), sensing a radio-frequency identification (RFID) signature, sensing the electronic signature of another computing device (e.g., a mobile phone associated with the individual) or a medication container, etc.

The motion sensor 508 (as well as any other sensors) can be coupled to the power supply 512. The power supply 512 may include a battery, a replaceable/rechargeable battery pack, a solar cell, some other regenerative power source, or any combination thereof. For example, the power supply 512 may be a set of rechargeable lithium ion batteries. The rechargeable lithium ion batteries may be adapted to be recharged via a physical charging interface that includes one or more electrical contacts for contact charging. For example, the electrical contact(s) may be designed to mate with corresponding electrical contact(s) of a charging apparatus, such as a base station, cable, or another computing device. Additionally or alternatively, the power supply 512 may support wireless charging.

In some embodiments, the universal modular attachment 500 includes an optical sensor (e.g., a camera) that is used to visually record activities during administration of the medication. For example, the optical sensor may be configured to record medication management activities, such as opening the eye drop container, dispensing eye drops, etc. As another example, the optical sensor could be configured to record an image/video before or after administration of the medication. Additionally or alternatively, a depth sensor or an image sensor (e.g., configured for thermal imaging, radar, or sonar) may be used to discover characteristic(s) of the ambient environment.

The universal modular attachment 500 also includes a housing that can be made of food grade material(s) and/or water-resistant material(s). For example, the universal modular attachment 500 may include a plastic housing that is encapsulated by a flexible, water-resistant rubber coating that improves cleanability and durability. Other embodiments of the universal modular attachment 500 may include a housing comprised of rubber, metal, ceramic, etc. Some embodiments of the universal modular attachment 500 further comprise a smooth powder coating that provides a durable aesthetic finish. The housing of the universal modular attachment 500 and/or the powder coating may include an antimicrobial additive that inhibits the growth and development of microorganisms.

Figure 6:
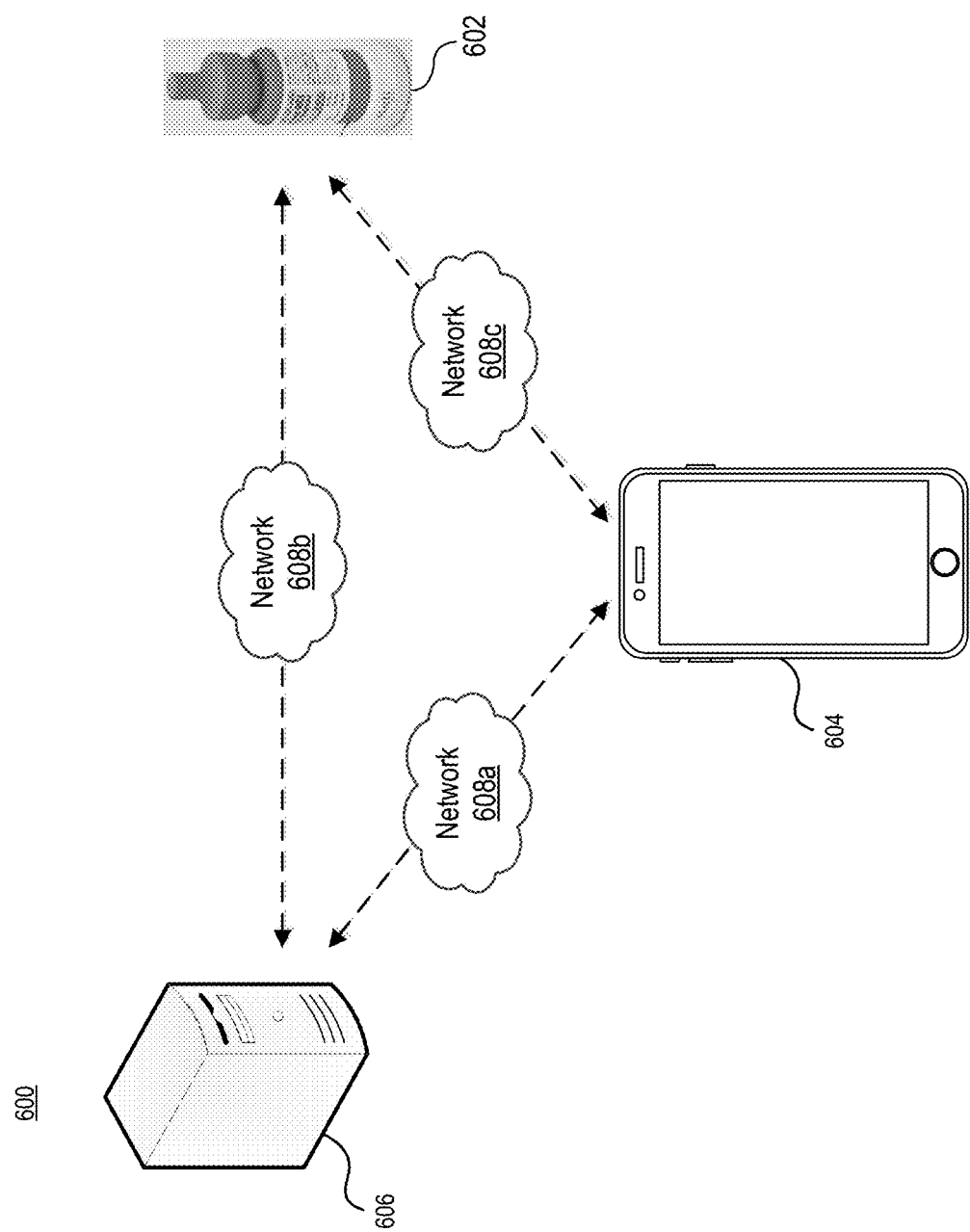
FIG. 6 depicts an example of a network environment that includes a universal modular attachment, a mobile phone having an application configured to present an adherence report, and a network-accessible server system responsible for supporting the application.

FIG. 6 depicts an example of a network environment 600 that includes a universal modular attachment 602, a mobile phone 604 having an application configured to present an adherence report, and a network-accessible server system 606 responsible for supporting the application. However, in some embodiments the network environment 600 may only include a subset of these computing devices (e.g., only the universal modular attachment 602 and the network-accessible server system 606).

While embodiments described herein may involve mobile phones, those skilled in the art will recognize that such embodiments have been selected for the purpose of illustration only. The technology could be used in combination with any computing device that is able to communicate with the universal modular attachment 602 and/or the network-accessible server system 606, such as personal computers, tablet computers, personal digital assistants (PDAs), game consoles (e.g., Sony PlayStation® or Microsoft Xbox®), music players (e.g., Apple iPod Touch®), wearable electronic devices (e.g., watches or fitness bands), network-connected ("smart") devices (e.g., televisions and home assistant devices), virtual/augmented reality systems (e.g., head-mounted displays such as Oculus Rift® and Microsoft Hololens®), or other electronic devices.

The universal modular attachment 602, mobile phone 604, and/or network-accessible server system 606 can be connected via one or more networks 608a-c, which may include the Internet, local area networks (LANs), wide area networks (WANs), metropolitan area networks (MANs), cellular networks (e.g., LTE, 3G, 4G), etc. Additionally or alternatively, the universal modular attachment 602, mobile phone 604, and/or network-accessible server system 606 may communicate with one another over a short-range communication protocol, such as Bluetooth®, Near Field Communication (NFC), radio-frequency identification (RFID), wireless Universal Serial Bus (USB), a proprietary point-to-point protocol, etc. Thus, the universal modular attachment 602 can be coupled to the mobile phone 604 and/or the network-accessible server system 606 via a wired channel or a wireless channel.

Generally, a mobile application executing on the mobile phone 604 is responsible for generating and/or presenting an adherence report that indicates whether an individual has administered medication from an eye drop container connected to the universal modular attachment 602 in accordance with a medication regimen. In some embodiments the mobile phone 604 is responsible for processing data generated by sensor(s) included in the universal modular attachment 602, while in other embodiments some or all of the processing is performed by the universal modular attachment 602. Therefore, in some instances the universal modular attachment 602 may execute the techniques described herein without needing to be communicatively coupled to any network(s), other computing device(s), etc.

In some embodiments the network-accessible server system 606 is responsible for supporting the application executing on the mobile phone 604, while in other embodiments the network-accessible server system 606 acts as a repository for sensor data generated by the universal modular attachment 602. The network-accessible server system 606 may also include algorithms that can be applied by the universal modular attachment 602 and/or the mobile phone 604 to more intelligently parse the sensor data.

Figure 7:
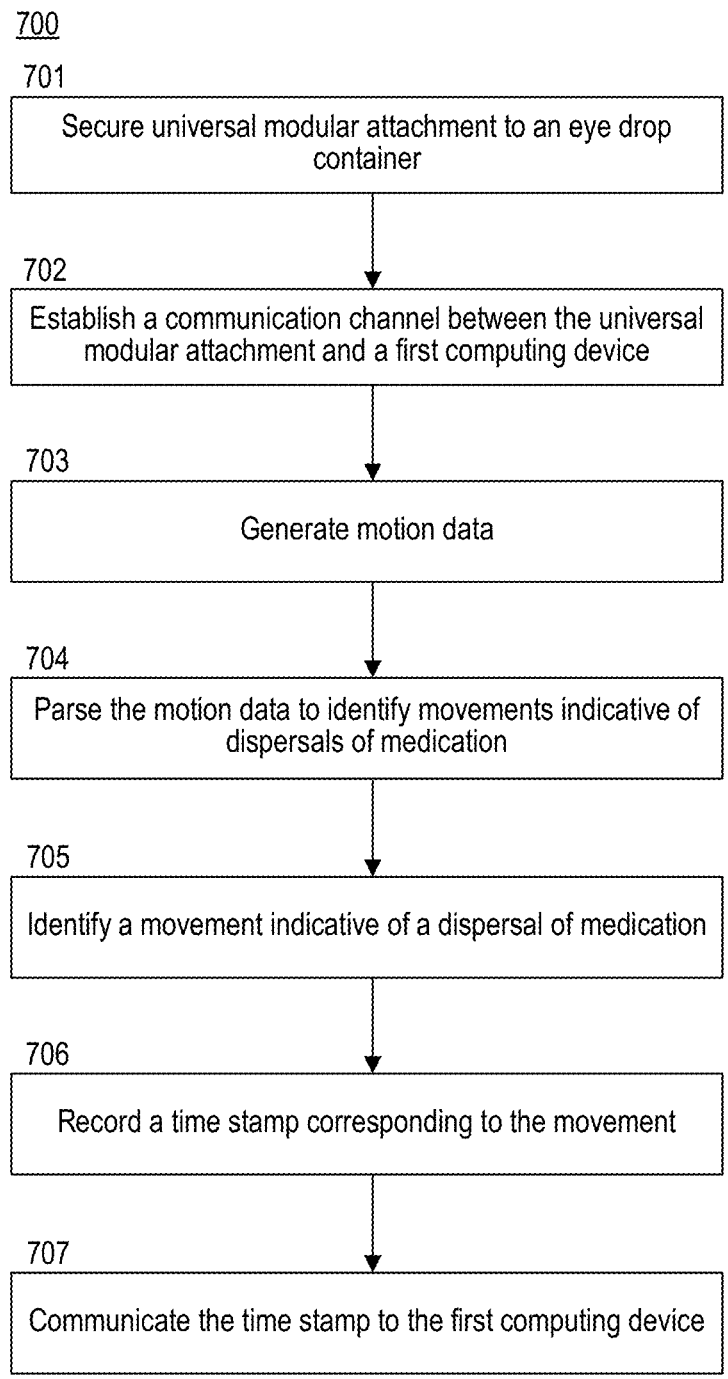
FIG. 7 is a flow diagram of a process for detecting administrations of medication (e.g., eye drops) from a container and/or monitoring adherence to a medication regimen.

FIG. 7 is a flow diagram of a process 700 for detecting administrations of medication (e.g., eye drops) from a container and/or monitoring adherence to a medication regimen. A universal modular attachment is initially secured to an eye drop container (step 701). Generally, the universal modular attachment is detachably connected to a connector ring that is fixedly attached to the eye drop container. However, the universal modular attachment could also be connected directly to the eye drop container.

The universal modular attachment can then establish a communication channel between itself and a first computing device (step 702). For example, a wireless communication module housed within the universal modular attachment could establish a communication channel using the Near Field Communication (NFC) protocol, wireless Universal Serial Bus (USB) protocol, Bluetooth® protocol, WiFi protocol, or a proprietary point-to-point protocol.

A motion sensor housed within the universal modular attachment can then generate motion data (step 703). Because the universal modular attachment is secured to the eye drop container, the motion data represents the collective motion of both items.

The universal modular attachment can then parse the motion data to identify movements that are indicative of dispersals of medication from the eye drop container (step 704). A processor may be configured to parse some or all of the motion data generated by the motion sensor. In some instances, the universal modular attachment (and, more specifically, the processor) will identify a movement indicative of a dispersal of medication from the eye drop container (step 705). For example, the processor may detect variations in the motion data that indicate the eye drop container was picked up, shaken, inverted, squeezed, etc.

In some embodiments, the universal modular attachment then records a time stamp corresponding to the movement (step 706). Other information could also be recorded, including ambient information (e.g., temperature, humidity, pollution), health information (e.g., by prompting the individual to specify side effects, present condition, etc.), device information (e.g., battery level), etc.

The universal modular attachment can then communicate the time stamp to the first computing device (step 707). In some embodiments the first computing device examines the time stamp to determine whether the medication was administered in accordance with a medication regimen, while in other embodiments the universal modular attachment is responsible for determining compliance.

Unless contrary to physical possibility, it is envisioned that the steps described above may be performed in various sequences and combinations. For example, the wireless communication module of the universal modular attachment may not establish the communication channel until after movement(s) have been identified within the motion data. As another example, some embodiments of the universal modular attachment periodically (e.g., daily or weekly) upload time stamps and/or motion data to the first computing device, while other embodiments of the universal modular attachment automatically sync with the first computing device so long as both devices are communicatively coupled to one another (e.g., connected to the same network).

Other steps could also be included. For example, some embodiments of the universal modular attachment further transmit an indication of the dispersal of medication to the first computing device. Reception of the indication may prompt the first computing device to determine a compliance level for an individual based on whether the dispersal(s) satisfy parameters of a medication regimen, and then transmit a notification to a second computing device that specifies the compliance status. The first computing device may be a network-accessible server system or a personal computing device associated with the individual, while the second computing device may be a personal computing device associated with the individual or another individual (e.g., family member, medical professional, or researcher).

As another example, a universal modular attachment could include an ambient sensor (e.g., temperature sensor, humidity sensor, pollution sensor) that generates data that characterizes the ambient environment. In such embodiments, the universal modular attachment could parse the data to detect one or more features that enable the medication regimen to be personalized for an individual, update a parameter for administering the medication, and notify the individual of the updated parameter. For example, the universal modular attachment may increase the number of eye drops to be administered responsive to determining that the ambient environment is warmer or drier than a specified threshold. Notifications can be delivered via an electronic display, light-emitting diodes (LEDs), speaker, haptic actuator, etc. Moreover, notifications may be in the form of an email message, text message, push notification, automated voice message, etc.

Processing System

Figure 8:
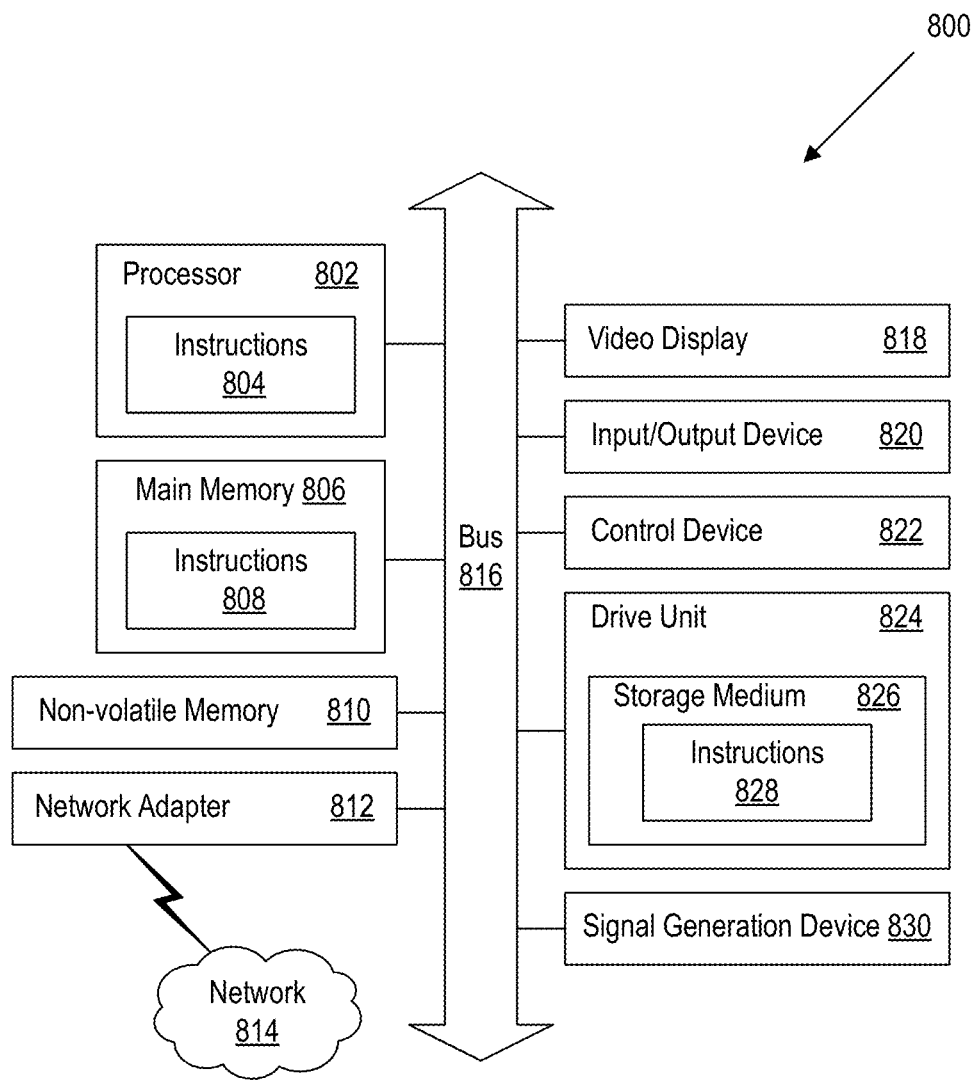
FIG. 8 is a block diagram illustrating an example of a processing system in which at least some operations described herein can be implemented.

FIG. 8 is a block diagram illustrating an example of a processing system 800 in which at least some operations described herein can be implemented. The processing system may include one or more central processing units ("processors") 802, main memory 806, non-volatile memory 810, network adapter 812 (e.g., network interfaces), video display 818, input/output devices 820, control device 822 (e.g., keyboard and pointing devices), drive unit 824 including a storage medium 826, and signal generation device 830 that are communicatively connected to a bus 816.

The bus 816 is illustrated as an abstraction that represents one or more physical buses and/or point-to-point connections that are connected by appropriate bridges, adapters, or controllers. Therefore, the bus 816 can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

In some embodiments the processing system 800 operates as part of a universal modular attachment configured to track administrations of medication, while in other embodiments the processing system 800 is connected (wired or wirelessly) to the universal modular attachment. In a networked deployment, the processing system 800 may operate in the capacity of a server or a client machine in a client-server network environment, or as a peer machine in a peer-to-peer network environment. The processing system 800 may be a server, a personal computer (PC), a tablet computer, a laptop computer, a personal digital assistant (PDA), a mobile phone, a processor, a telephone, a web appliance, a network router, a switch, a bridge, a console, a gaming device, a music player, or any machine capable of executing a set of instructions (sequential or otherwise) that specify actions to be taken by the processing system 800.

While the main memory 806, non-volatile memory 810, and storage medium 826 (also called a "machine-readable medium") are shown to be a single medium, the term "machine-readable medium" and "storage medium" should be taken to include a single medium or multiple media (e.g., a centralized or distributed database and/or associated caches and servers) that store one or more sets of instructions 828. The term "machine-readable medium" and "storage medium" shall also be taken to include any medium that is capable of storing, encoding, or carrying a set of instructions for execution by the processing system 800.

In general, the routines executed to implement the embodiments of the disclosure may be implemented as part of an operating system or a specific application, component, program, object, module or sequence of instructions referred to as "computer programs." The computer programs typically comprise one or more instructions (e.g., instructions 804, 808, 828) set at various times in various memory and storage devices in a computing device, and that, when read and executed by the one or more processors 802, cause the processing system 800 to perform operations to execute elements involving the various aspects of the technology.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include, but are not limited to, recordable-type media such as volatile and non-volatile memory devices 810, floppy and other removable disks, hard disk drives, optical disks (e.g., Compact Disk Read-Only Memory (CD ROMS), Digital Versatile Disks (DVDs)), and transmission-type media such as digital and analog communication links.

The network adapter 812 enables the processing system 800 to mediate data in a network 814 with an entity that is external to the processing system 800 through any communication protocol supported by the processing system 800 and the external entity. The network adapter 812 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 812 can include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of, for example, one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

Although the above Detailed Description describes certain embodiments and the best mode contemplated, no matter how detailed the above appears in text, the embodiments can be practiced in many ways. Details of the technology may vary considerably in its implementation details while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments covered by the claims.

The language used in the specification has been principally selected for readability and instructional purposes, and it may not have been selected to delineate or circumscribe the inventive subject matter. It is therefore intended that the scope of the invention not be limited by this Detailed Description, but rather by any claims that issue on an application based hereon. Accordingly, the disclosure of various embodiments is intended to be illustrative, but not limiting, of the scope of the technology.

What is claimed is:

1. A modular attachment for detecting administrations of medication, the modular attachment comprising:
    a housing that is detachably connectable to a connector ring fixedly attached to a bottom of a container of medication;
    a motion sensor configured to detect instances of movement that are indicative of dispersals of medication from the container;
    a power supply;
    a memory configured to store motion data generated by the motion sensor; and
    a wireless communicator configured to exchange information bi-directionally with a computing device across a network,
    wherein the connector ring is attached to the container in a position spaced apart from a dispensing path for dispersing medication from the container, and
    wherein the modular attachment is configured to be spaced apart from the dispensing path when the housing is connected to the connector ring.

2. The modular attachment of claim 1, further comprising:
    a magnet disposed within the housing,
    wherein the magnet maintains the modular attachment in a predetermined orientation relative to the container when the modular attachment is positioned proximate to a complementary magnet included in the connector ring.

3. The modular attachment of claim 1, wherein the housing includes a threaded portion designed to mate with a complementary threaded portion of the connector ring.

4. The modular attachment of claim 1, wherein the bi-directional exchange is accomplished using any of a Near Field Communication (NFC) protocol, a wireless Universal Serial Bus (USB) protocol, a Bluetooth protocol, a WiFi protocol, a cellular data communication protocol, and a proprietary point-to-point protocol.

5. The modular attachment of claim 1, further comprising:
    an electrical contact connected to the power supply that extends through the housing,
    wherein the electrical contact receives power upon initiating and maintaining a physical connection with a corresponding electrical contact of a charging apparatus.

6. The modular attachment of claim 1, wherein the housing further comprises:
    a flexible, water-resistant coating that improves cleanability and durability.

7. The modular attachment of claim 6, wherein the flexible, water-resistant coating includes an antimicrobial additive that inhibits growth and development of microorganisms.

8. The modular attachment of claim 1, wherein the housing is comprised of plastic, rubber, metal, ceramic, or some combination thereof.

9. The modular attachment of claim 1, further comprising:
    an audio sensor configured to record a response uttered by an individual;
    a light sensor configured to monitor an ambient light level;
    a humidity sensor configured to monitor an ambient humidity level;
    a temperature sensor configured to monitor an ambient temperature; or
    an electromagnetic sensor configured to monitor an ambient electromagnetic radiation level.

10. An apparatus for detecting administrations of medication, the apparatus comprising:
a connector ring fixedly attached to a bottom of a container of medication such that the connector ring is spaced apart from a dispensing path that allows medication to be administered from the container;
a modular attachment including—
a housing that is detachably connectable to the connector ring,
a motion sensor configured to detect instances of movement that are indicative of dispersals of medication from the container, and
a wireless communicator configured to exchange information bi-directionally with a computing device across a network; and
a first sensor affixed to an outer surface of the container, wherein an output of the first sensor is operatively coupled to the modular attachment,
wherein the modular attachment is configured to be positioned separate from the dispensing path when the housing is connected to the connector ring.

11. The apparatus of claim 10, wherein the first sensor is disposed beneath a label sticker affixed to the container.

12. The apparatus of claim 10, wherein the first sensor is a piezoelectric sensor configured to detect structural deformations of the container caused by an individual dispensing medication.

13. The apparatus of claim 10, wherein the first sensor is a pressure sensor configured to detect variations in pressure caused by an individual grasping the container.

14. The apparatus of claim 10, further comprising:
a second sensor configured to detect when the modular attachment has been attached to the connector ring.

15. The apparatus of claim 14, wherein the second sensor is selected from:
an optical sensor that detects when a portion of the modular attachment has been placed within a cavity of the connector ring; and
a pressure sensor upon which pressure is exerted when the portion of the modular attachment is secured within the cavity of the connector ring.

16. The apparatus of claim 10, further comprising:
an electronic display configured to display information regarding the medication, a medication regimen, or both.

17. The apparatus of claim 10, further comprising:
one or more light-emitting diodes (LEDs) that visually convey information to an individual that is responsible for administering medication from the container.

18. The apparatus of claim 10, further comprising:
an audio sensor configured to generate an audio signal responsive to an individual providing audio input; and
a speaker that audibly conveys information to the individual that is responsible for administering medication from the container.

19. The apparatus of claim 10, wherein the housing of the modular attachment is detachably connectable to connector rings corresponding to containers of different sizes.

20. A computer-implemented method comprising:
establishing, by a wireless communicator of a modular attachment, a communication channel between the modular attachment and a first computing device,
wherein the modular attachment is affixed to a container from which medication can be dispensed such that the modular attachment is spaced apart from medication as the medications is dispensed from the container, via a connector ring fixedly attached to a bottom of the container;
generating, by a motion sensor of the modular attachment, motion data representing collective movement of the modular attachment and the container;
parsing, by a processor of the modular attachment, the motion data to identify movements that are indicative of dispersals of medication from the container;
identifying, by the processor of the modular attachment, a movement indicative of a dispersal of medication from the container;
recording, by the processor of the modular attachment, a time stamp corresponding to the movement; and
communicating, by the wireless communicator of the modular attachment, the time stamp to the first computing device, which determines whether the medication was administered in accordance with a medication regimen.

21. The computer-implemented method of claim 20, further comprising:
transmitting, by the wireless communicator of the modular attachment, an indication of the dispersal of medication to the first computing device across a network,
wherein reception of the indication prompts the first computing device to determine a compliance level for an individual based on whether dispersals of medication from the container satisfy parameters of the medication regimen, and
transmit a notification to second computing device that specifies the compliance status.

22. The computer-implemented method of claim 21, wherein the first computing device is included in a network-accessible server system, and the second computing device is associated with the individual.

23. The computer-implemented method of claim 21, wherein the first computing device is associated with the individual, and wherein the second computing device is associated with another individual.

24. The computer-implemented method of claim 20, further comprising:
recording, by an ambient sensor of the modular attachment, ambient data that characterizes an ambient environment;
parsing, by the processor of the modular attachment, the ambient data to detect one or more features that enable the medication regimen to be personalized for an individual;
updating, by the processor of the modular attachment, a parameter for administering the medication; and
notifying the individual of the updated parameter.

25. The computer-implemented method of claim 24, wherein said notifying is performed an email message, a text message, a push notification, or an automated voice message.

26. An apparatus comprising:
a connector ring adapted to be fixedly engaged with a bottom of a medication container such that the connector ring is spaced apart from a medication dispensing path;
a modular attachment, comprising:
a housing adapted to be removably engaged with the connector ring such that the housing is separate from the medication dispensing path, the housing comprising:

a motion sensor configured to detect instances of movement that are indicative of dispersals of medication from the container;
a power supply;
a memory configured to store motion data generated by the motion sensor; and
a wireless communicator configured to exchange information bi-directionally with a computing device across a network;
wherein active elements for detecting administrations of medication by the modular attachment are separate from the connector ring.

* * * * *